United States Patent [19]
Lücke et al.

[11] Patent Number: 5,589,977
[45] Date of Patent: Dec. 31, 1996

[54] BINOCULAR TUBE ASSEMBLY FOR A STEREOMICROSCOPE

[75] Inventors: Christian Lücke, Oberkochen; Uwe Vry, Aalen; Ulrich Lemcke, Heidenheim, all of Germany

[73] Assignee: Carl-Zeiss-Stiftung, Heidenheim-Brenz, Germany

[21] Appl. No.: 406,400

[22] Filed: Mar. 20, 1995

[30] Foreign Application Priority Data

Mar. 24, 1994 [DE] Germany ............... 44 10 147.3

[51] Int. Cl.⁶ .......................................... G02B 21/20
[52] U.S. Cl. ............................ 359/375; 359/377
[58] Field of Search ........................ 359/368, 375, 359/376, 377, 378, 381

[56] References Cited

U.S. PATENT DOCUMENTS 4,175,826  11/1979  Blaha et al. ................. 359/377
4,798,451   1/1989  Fujiwara ..................... 359/375

FOREIGN PATENT DOCUMENTS 9308044  9/1993  Germany.

Primary Examiner—Timothy P. Callahan
Assistant Examiner—Jeffrey Zweizig
Attorney, Agent, or Firm—Walter Ottesen

[57] ABSTRACT

A prism component group is provided in a pivotable binocular tube assembly for a stereomicroscope. The prism component group is configured as a deflection prism with two roof prisms cemented thereto. The two roof prisms are offset relative to respective ones of the optical axes of the stereoscopic component beam paths.

15 Claims, 4 Drawing Sheets

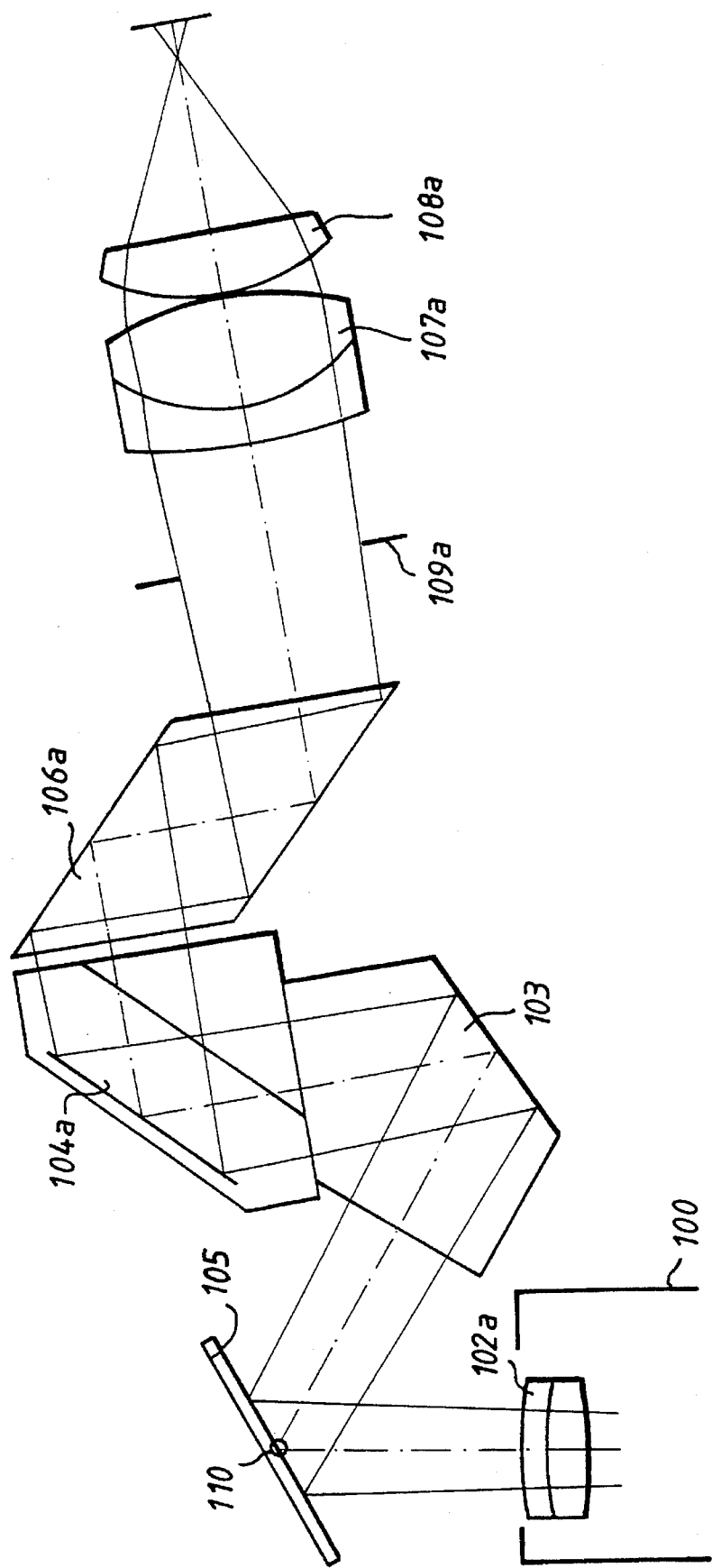

BINOCULAR TUBE ASSEMBLY FOR A STEREOMICROSCOPE

BACKGROUND OF THE INVENTION

Binocular tube assemblies for stereomicroscopes wherein optical beams are folded are, for example, utilized in surgical microscopes. There, the shortest possible working distance between the viewing end of the microscope and the object to be viewed is necessary for large focal intercepts of the main objective. This is necessary in order that the surgeon can assume a relaxed body position during surgery.

It is furthermore desirable in surgical microscopes to provide the possibility of a continuous change off the viewing angle between the housing of the stereomicroscope and the binocular tube assembly. Also, such a binocular tube assembly should provide for adjusting the eye spacing.

A binocular tube assembly which basically satisfies these requirements is disclosed, for example, in U.S. Pat. No. 4,175,286. The binocular tube assembly described here is mounted to be rotatable about a pivot axis disposed perpendicularly to the optical axis of the stereoscopic component beam paths. A deflecting mirror is likewise mounted to be rotatable about the pivot axis. When the binocular tube assembly is pivoted, the deflecting mirror is entrained to rotate therewith by half the pivot angle. A first group off optical deflecting elements follows the rotatable deflecting mirror. This first group deflects the component beam paths coming from the deflecting mirror in the direction of a second group of deflecting elements. Both deflecting element groups can be pivoted together with the binocular tube assembly. Furthermore, and after the second group of deflecting elements, rhombic prisms are arranged in the stereoscopic component beam paths so as to be rotatable about the particular optical axis in order to permit a selective adjustment of the eye distance. The oculars are, in turn, mounted in the component beam paths after the rhombic prisms.

The desire for an ergonomically more favorable pivot range than is realizable with a binocular tube assembly of this kind has resulted, inter alia, in increasing requirements on the work ergonomics. At times, another relative orientation of the binocular tube assembly to the housing of the stereomicroscope is also sought.

The binocular tube assembly disclosed in U.S. Pat. No. 4,175,826 includes an optic component which comprises a prism group having lenses cemented to each end. Such an optical component imposes high requirements with respect to manufacture.

A further binocular tube assembly for a stereomicroscope is disclosed in U.S. Pat. No. 4,798,451. The optical image deflecting elements utilized in this binocular tube assembly comprise mirror-prism combinations which are similar to the beam path trace of portoprisms of the second order. These portoprisms, however, require considerable space and overall lead to a correspondingly wide configuration of the entire binocular tube assembly which sometimes is disturbing to the viewer. Furthermore, relatively long glass and air paths result for an assembly of this kind. Finally, separate deflecting elements in the form of separate pivot mirrors are provided for corresponding ones of the stereoscopic component beam paths. The pivot mirrors therefore also have to be separately adjusted. A very considerable effort for adjustment is therefore necessary.

Furthermore, two component lenses are required in each of the stereoscopic component beam paths in the above-described binocular tube assembly. This, in turn, leads to a very disadvantageous position of the pupils.

A further variation of the binocular tube assembly of the kind described above for stereomicroscopes is disclosed in German published utility registration G 9,308,044.1. The image reversal is here made with the portoprisms of the second order. These optical image reversal elements are very voluminous for large pupil diameters and correspondingly large intermediate images. Also, the possibility of adjustment for the required variable pupil distance with a binocular tube assembly of the kind described in this publication is most complex and can hardly be realized.

SUMMARY OF THE INVENTION

It is an object of the invention to avoid the disadvantages of the state of the art referred to above. In addition to an ergonomic situation as optimal as possible for the observer, a good imaging quality without vignetting occurring in the binocular tube assembly is especially desirable. Likewise, the complexity of adjustment and manufacture is reduced.

The binocular tube assembly of the invention is for a stereomicroscope and defines at least two stereoscopic component beam paths along first and second optical axes, respectively. The binocular tube assembly includes: two sets of ocular optics; pivot means for pivotally mounting the sets of ocular optics to pivot relative to the stereomicroscope through a pregiven angular range; a prism component group including a deflecting prism having an entry face for receiving the component beam paths therein and an exit face through which the component beam paths leave the prism; and, two image-reversing roof prisms mounted on one of the faces so as to be offset relative to respective ones of the optical axes; and, an optical deflecting element common to both of the component beam paths and being mounted on the pivot means for deflecting the component beams toward the sets of ocular optics, respectively, for all positions of the ocular optics within the angular range.

According to a feature of the invention, a prism component group is provided in the binocular tube which essentially comprises a deflection prism having two roof prisms mounted on the exit and entry faces of the deflection prism. The two roof prisms function as separate image reversing elements and are, in addition, mounted so as to be offset with respect to the optical axes of the entering stereoscopic component beam paths. From this, an increase of the distance of the two optical axes of the stereoscopic component beam paths occurs after passing through these optical elements. The adjustment of the pupil distance with the aid of rotatable rhombic prisms is significantly facilitated in this manner because correspondingly more space is available for rotating these elements.

Overall, an adequate pivot range of the binocular tube assembly according to the invention results in an angle interval off 50°; that is, an angle interval which corresponds to good ergonomic conditions for the operating surgeon.

A reduction of the adjusting effort as well as a reduction of the manufacturing complexity is achieved in one embodiment of the invention when compared to the state of the art because, for each beam path, only one achromatic component lens is required.

Furthermore, the concept of the binocular tube assembly of the invention permits larger diameters of the intermediate image, which is viewed with the oculars, without vignetting occurring for the observer as an unwanted consequence.

In another embodiment of the invention, the binocular tube assembly can be pivoted out of a so-called straight viewing position. It is here understood that a straight-viewing position is a position off the binocular tube assembly wherein the viewing direction through the binocular tube assembly is aligned parallel to the optical axis off the stereomicroscope. A tube of this kind is very short because of the invention. More specifically, the working distance between the viewed object and the microscope entrance can be significantly minimized for a stretched orientation of the microscope and ocular axes. dr

BRIEF DESCRIPTION OF THE DRAWINGS

The invention will now be described with reference to the drawings wherein:

FIG. 4 shows the principal beam path and the arrangement of essential elements in a second embodiment of the binocular tube assembly of the invention; and, FIG. 5 is a side elevation view, partially in section, and shows the beam path and the arrangement of essential elements of a third embodiment of the binocular tube assembly of the invention wherein the binocular tube assembly can be pivoted out of a straight-viewing position.

DESCRIPTION OF THE PREFERRED EMBODIMENTS OF THE INVENTION

Figure 1:
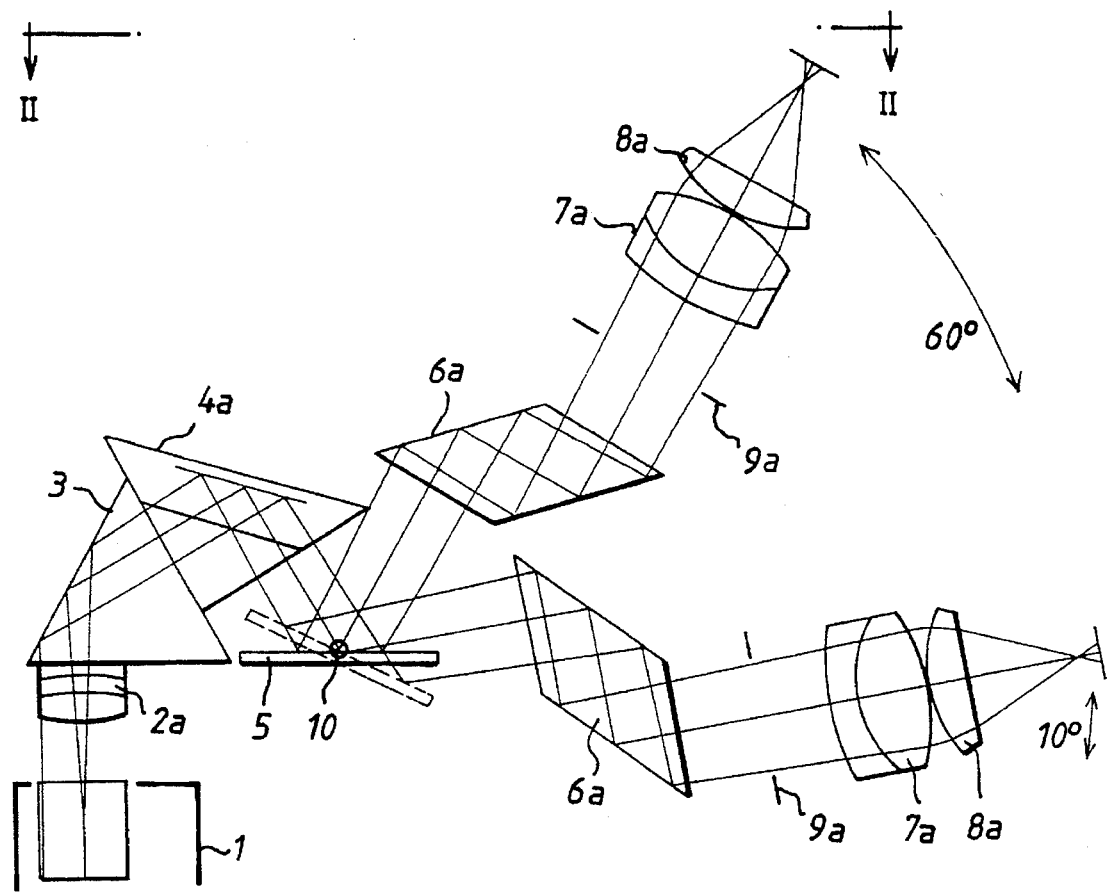
FIG. 1 shows the principal beam path and the arrangement of the essential elements of a first embodiment of the binocular tube assembly according to the invention in two pivot positions.

FIG. 1 shows a side elevation view of the essential elements of a first embodiment of the binocular tube assembly of the invention. Two pivot positions are shown which define the two extreme pivot positions.

The stereoscopic component beam paths pass via tile optical system of the actual stereomicroscope into the binocular tube assembly of the invention. The two parallel stereoscopic component beam paths pass through two barrel lenses 2a, respectively, forward of the binocular tube assembly. The barrel lenses 2a are also known as tubular objectives and only one thereof is shown.

The optical system (not shown) of the stereomicroscope includes a known optical configuration including a main objective and a downstream magnification-change device.

Figure 2:
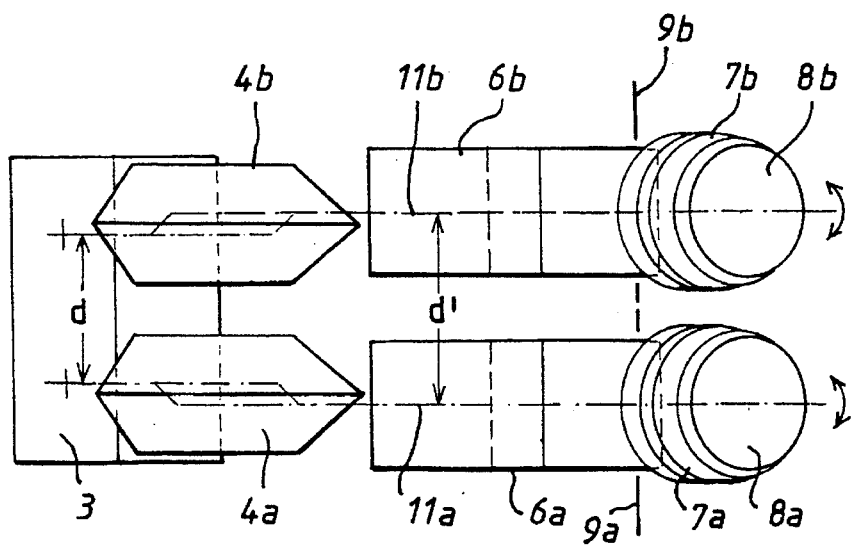
FIG. 2 is a plan view of the optical elements of the binocular tube assembly of FIG. 1.

Two parallel stereoscopic component beam paths leave the housing 1 of the stereomicroscope and thereafter enter the binocular tube assembly. In the embodiment shown of the binocular tube assembly, a prism component group (3, 4a, 4b) follows the barrel lenses 2a. The prism component group (3, 4a, 4b) comprises a deflection prism 3 as well as two roof prisms (4a, 4b) mounted on the exit face of the deflecting prism 3 as shown in FIGS. 1 and 2. In FIG. 1, only the left-hand stereoscopic beam path (as viewed by the observer) is shown and the optical elements mounted therein can be seen.

Figure 3A:
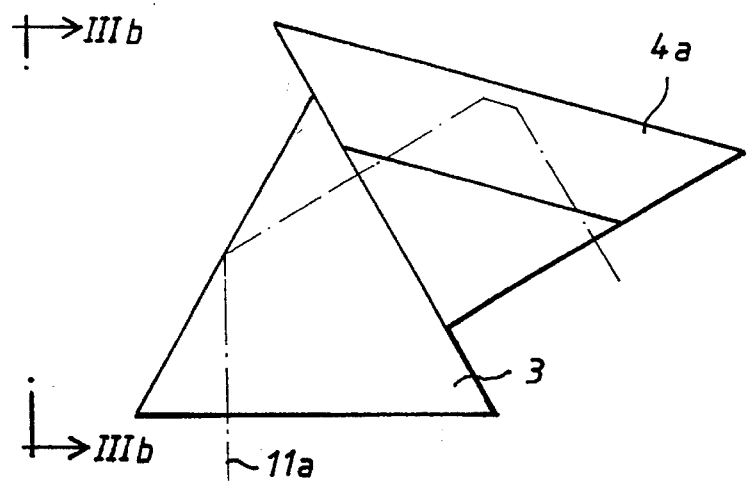
FIGS. 3a to 3c show respective views of the prism component groups of the binocular tube assembly of FIGS. 1 and 2.
Figure 3B:
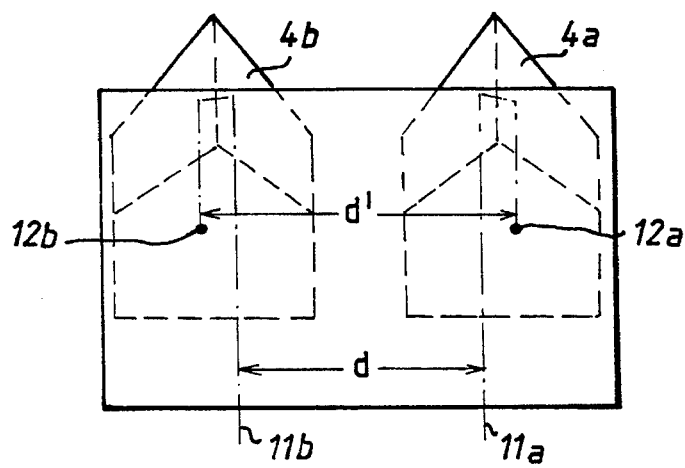
Figure 3C:
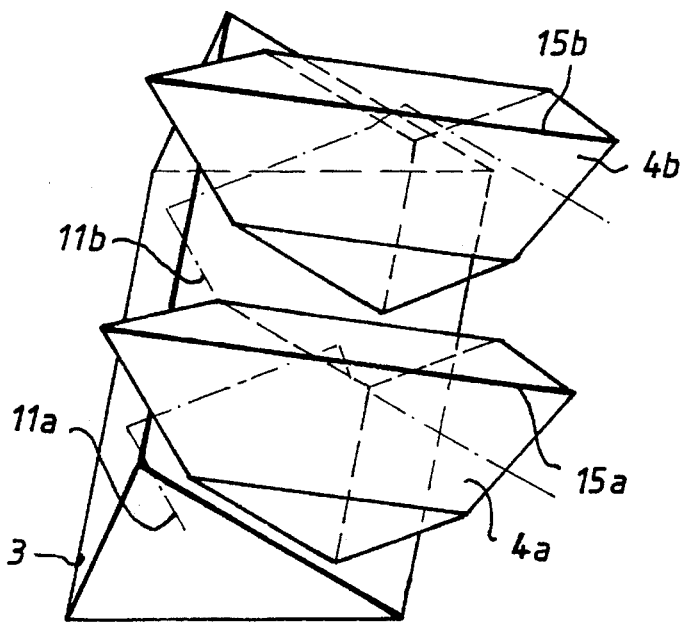

The deflecting prism 3 is configured as a 60° prism in the embodiment shown and is used in common by the two stereoscopic component beam paths. The exit face of the deflecting prism 3 is arranged so that it is orientated in the direction of the ocular. In the embodiment shown, a 90° roof prism (4a or 4b) is mounted on the exit face of the deflecting prism 3 in each of the two stereoscopic component beam paths. Reference can be made to FIGS. 3a to 3c for a detailed explanation of the operation of the entire prism component group (3, 4a, 4b) of this embodiment of the binocular tube assembly.

The image is reversed in the prism component group (3, 4a, 4b) or more specifically, in the two roof prisms (4a, 4b). Thereafter, the stereoscopic component beams reach a rotatably mounted deflection element 5 which, in turn, is utilized in common by the two stereoscopic component beam paths. In the embodiment shown, a rectangularly-shaped mirror is provided as the deflecting element 5. The deflection element 5 is mounted so that it can rotate about pivot axis 10 which corresponds to the pivot axis of the entire binocular tube assembly of the invention. Other reflecting optical elements can be used as an alternative to the rotatably mounted deflection mirror 5.

The mounted optical elements of the binocular tube assembly, which follow along the stereoscopic component beam paths, are connected to the deflecting element 5 in a defined orientation. These optical elements include, in a first one of the stereoscopic component beam paths: rhombic prism 6a, viewing field diaphragm 9a and ocular lenses (7a, 8a) and, in a second one of the stereoscopic component beam paths: the rhombic prism 6b, the viewing field diaphragm 9b and the ocular lenses (7b, 8b).

In FIG. 1, two possible extreme pivot positions of the first embodiment of the binocular tube assembly are shown. It can be clearly seen here that the prism component group (3, 4a, 4b) has a definite fixed orientation with respect to the housing 1 of the stereoscopic microscope in each pivot position. On the other hand, the deflection element 5 and the two sets of optical elements (6a, 9a, 7a, 8a) and (6b, 9b, 7b, 8b) have a defined orientation relative to each other and are pivotable as a unit with respect to the housing 1 of the stereomicroscope.

The angles correspond to the two pivot positions. The two angles are conjointly defined by the component beam paths and the horizontal and are 60° and 10°, respectively. Accordingly, the binocular tube assembly of this embodiment allows for a pivot movement in an angular range of 50°. As disclosed in U.S. Pat. No. 4,175,826, the deflecting element 5 is journalled so that it can be rotated about the pivot axis 10 and, when pivoted, is entrained by the binocular tube assembly so that it Eotates half of the pivot angle. In this way, for a pivot angle range of the binocular tube assembly of 50°, an angular interval of 25° is provided in which the deflection element 5 can be rotated.

A plan view of the arrangement of the individual optical elements off the first embodiment of the binocular tube assembly of the invention is shown in FIG. 2. The configuration of the prism component group (3, 4a, 4b) comprises the commonly utilized deflection prism 3 and the two 90° roof prisms (4a, 4b) which are cemented to the exit face of the deflection prism 3.

The roof prisms (4a, 4b) produce a beam offset of each of the two optical axes (11a, 11b) of the entering stereoscopic component beam paths. The optical axes (11a, 11b) of the stereoscopic component beam paths are displaced outwardly after passing through the roof prisms (4a, 4b); that is, a greater spacing d' of the two optical axes (11a, 11b) results after passing through the prism component group (3, 4a, 4b) when compared to the spacing (d) when entering the prism component group (3, 4a, 4b). This axis offset δd=d'−d is advantageous because the clear diameter, which then becomes available, is increased for the two rhombic prisms (6a, 6b) and therefore more space is provided for rotating the two rhombic prisms (6a, 6b). In this way, the constructive configuration of the binocular tube assembly is significantly facilitated. The rotatability of the two rhombic prisms (6a, 6b) including the downstream sets of ocular lenses (7a, 8a; 7b, 8b) is required about the respective optical axes (11a, 11b) in order to ensure the desired adjustability of the eye spacing for the observer.

FIGS. 3a to 3c provide various views off the prism component groups utilized in the embodiment of FIGS. 1 and 2. FIG. 3a shows the side elevation view of the 60°-deflection prism 3 and the roof prism 4a which is the left-hand roof prism when viewed by the observer. The optical axis 11a of the entering left stereoscopic component beam path and the resulting reflections at the corresponding faces in the prism component group (3, 4a) are likewise shown in FIG. 3a.

A front view of the prism component group (3, 4a, 4b) is shown in FIG. 3b. Here, the resulting offset δd=d'−d of the optical axes (11a, 11b) after the stereoscopic component beam paths pass through the prism component group (3, 4a, 4b) can be clearly seen. The spacing d' of the two optical axes after passing through the prism component group (3, 4a, 4b) is significantly greater when compared to the spacing (d) of the optical axes (11a, 11b) when entering the commonly utilized deflection prism 3. Likewise, FIG. 3b shows the respective exit points (12a, 12b) of the optical axes from the two 90°-roof prisms (4a, 4b).

A perspective view of the prism component group (3, 4a, 4b) as well as of the optical axes (11a, 11b) of the stereoscopic component beam paths which pass through this group and the resulting reflections at the individual reflection faces are shown in FIG. 3c. FIG. 3c clearly shows the arrangement of the two 90°-roof prisms (4a, 4b) on the exit face of the commonly utilized deflection prism 3 which is orientated in the direction of the oculars. FIG. 3c also shows the configuration of the two roof prisms (4a, 4b) together with the respective roof edges (15a, 15b).

Accordingly, the image reversal required in the binocular tube assembly takes place therein in the roof prisms (4a, 4b) of the prism component group (3, 4a, 4b) described above. The configuration of this embodiment of the prism component group (3, 4a, 4b) permits a compact configuration as well as the desired increase of the spacing of the two optical axes (11a, 11b) of the stereoscopic component beam paths.

In addition to the selection of the deflection prism and the roof prisms mounted thereon described in the above embodiment, also alternative deflection prisms or prism arrangements having a roof edge for image reversal can be used according to the invention. What is essential in each case is the required image reversal based on an uneven number of occurring reflections and the resulting adjustment of the axes of the stereoscopic component beam paths.

Accordingly, the use of a so-called prism having imperfect roof edges is possible wherein no pupillary partition takes place by the roof edge; instead, a roof surface reflects the complete pupils. Here, requirements, which are not too high, are imposed on the manufacturing tolerances of the roof edge angle in order to satisfy the optical specifications.

A second embodiment of the binocular tube assembly for a stereomicroscope is shown in FIG. 4. Only the left-hand component beam path (as viewed from the observer) is shown.

The component beam paths coming from the optical system of the stereomicroscope pass through the barrel lenses (102a) and then reach the pivotally mounted deflecting element 105 which can be pivoted about pivot axis 110. The downstream mounted optical elements (103, 104a, 106a, 109a, 107a, 108a) of the binocular tube assembly are all connected in a fixed relative orientation to the deflecting element 105. The stereoscopic component beam paths are deflected via the deflecting element 105 and then reach a prism component group comprising a deflecting prism 103 which, in turn, is commonly used, as well as two roof prisms mounted on the deflecting prism 103. In FIG. 4, only one of the two roof prisms is shown, namely, prism 104a.

After image reversal in the roof prisms 104a, the stereoscopic component beam paths image upon the two rhombic prisms 106a mounted so as to be rotatable about the optical axes, respectively. The adjustment of the pupil distance of the observer is made with the rhombic prisms 106a. A viewing field diaphragm 109a and an ocular optic (107a, 108a) are mounted in the stereoscopic beam paths downstream of each of the rhombic prisms 106a.

As in tile first embodiment of FIGS. 1 to 3c, a compact prism component group (103, 104a) is mounted in the binocular tube assembly also in this embodiment. The prism component group (103, 104a), in turn, effects the desired increase of the spacing of the optical axes of the stereoscopic component beam paths and the required image reversal via the roof prisms.

Figure 5:
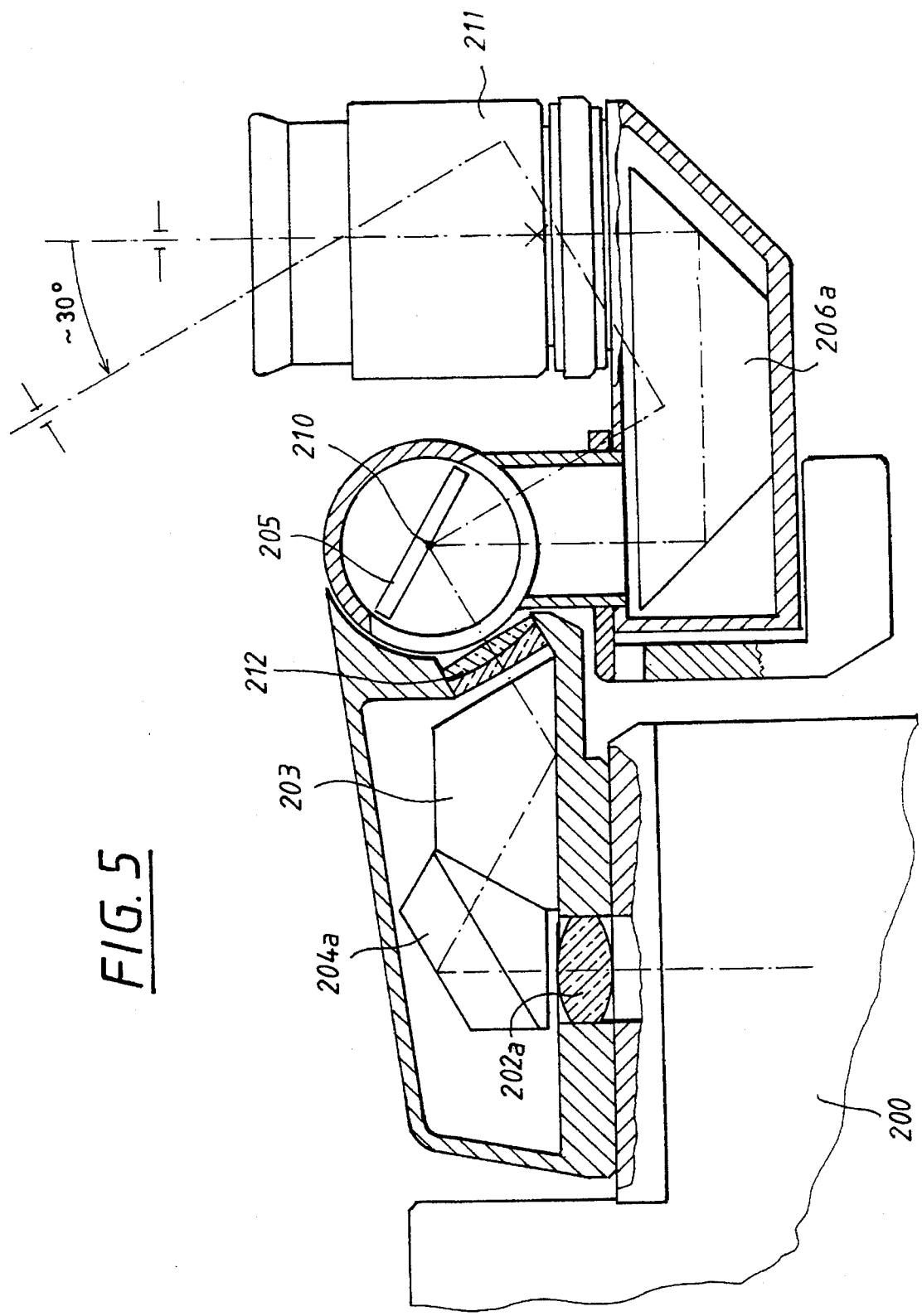

A third embodiment of the binocular tube assembly of the invention is shown in a side elevation view in FIG. 5. This embodiment is a binocular tube assembly which can be pivoted by a defined angular amount out of a so-called straight-view position. A straight-view position is here a position of the binocular tube assembly wherein the optical axes of the oculars are aligned parallel to the optical axis of the microscope. A binocular tube assembly of this kind is, for example, of advantage for a surgical microscope for use in neurosurgery.

The stereoscopic beam paths leave the housing 200 of the stereomicroscope and reach the prism component group, which is provided in fixed disposition to the housing 200, via the two barrel lenses 202a. Again, only one of the two barrel lenses 202a is shown in FIG. 5. The prism component group comprises a deflecting prism 203 as well as two roof prisms 204a mounted on the deflecting prism. Only one of the two roof prisms 204a is shown in FIG. 5.

In contrast to the two embodiments described above, the two roof prisms 204a are now mounted on the entry face of the deflecting prism 203. Accordingly, the stereoscopic component beam paths pass through the barrel lenses 202a and thereafter first pass through the two roof prisms 204a and are thereafter suitably deflected via the deflecting prism 203. The two roof prisms 204a are likewise mounted in the same way as in the embodiments described above in that a parallel offset outwardly s provided after the stereoscopic component beam paths pass through these prisms 204a.

The image reversal takes place in the two roof prisms 204a and, thereafter, the stereoscopic component beam paths pass via the deflecting prism 203 in the direction of the optical elements of the binocular tube assembly of the invention. These optical elements are mounted downstream of the deflecting prism 203. A further optical element in tile form of a composite lens 212 is provided in a fixed relative orientation to the barrel lenses 202a and the prism component group.

The movable part of this embodiment of the invention is, in turn, arranged downstream of the composite lens 212. The two stereoscopic component beam paths first impinge upon a deflecting element 205 in the form of a pivot mirror used in common by both stereoscopic component beam paths. The deflecting element 205 and the optical elements of the binocular tube assembly downstream thereof are rotatably journalled about an axis 210.

In the embodiment shown, a rotation of 30° out of the straight-viewing position is possible. In addition to the straight-viewing position, FIG. 5 also shows the position of the optical axis in the position after pivoting through 30°. The stereoscopic component beam paths are at least partially deflected back again into the direction of the viewed object via the deflecting element 205. In this way, a significant reduction of the overall length of this embodiment of the binocular tube assembly is realized.

The two 180° deflecting prisms 206a as well as the ocular lenses (not shown) in the two oculars 211 belong to the movable part of the binocular tube assembly. The two 180° deflecting prisms 206a, in turn, are movably journalled about an axis which is perpendicular to the longitudinal axis of the prism and permit the adjustment of the desired pupil distance by a corresponding rotation about this axis; that is, this axis is defined by that portion of the dash-dot optical axis of FIG. 5 extending between the deflecting element 205 and the 180° defelcting prism.

This embodiment of the binocular tube assembly of the invention provides an extremely short overall length of a stereomicroscope wherein the binocular tube assembly can be pivoted out of a straight-viewing position. This is especially advantageous when the shortest possible working distance between the surgical microscope and the patient is desired.

It is understood that the foregoing description is that of the preferred embodiments of the invention and that various changes and modifications may be made thereto without departing from the spirit and scope of the invention as defined in the appended claims.

What is claimed is:

1. A binocular tube assembly for a stereomicroscope defining at least two stereoscopic component beam paths along first and second optical axes, respectively, said binocular tube assembly comprising:

two sets of ocular optics;

pivot means for pivotally mounting said sets of ocular optics to pivot relative to said stereomicroscope through a pregiven angular range;

a prism component group including a deflecting prism having an entry face for receiving said component beam paths therein and an exit face through which said component beam paths leave said prism; and, two image-reversing roof prisms having respective roof edges, said roof prisms being mounted on one of said faces so as to cause said roof edges to be offset relative to respective ones of said optical axes; and, an optical deflecting element common to both of said component beam paths and being mounted on said pivot means for deflecting said component beams toward said sets of ocular optics, respectively, for all positions of said ocular optics within said angular range.

2. A binocular tube assembly for a stereomicroscope defining at least two stereoscopic component beam paths along first and second optical axes, respectively, said binocular tube assembly comprising:

two sets of ocular optics;

pivot means for pivotally mounting said sets of ocular optics to pivot relative to said stereomicroscope through a pregiven angular range;

a prism component group including a deflecting prism having an entry face for receiving said component beam paths therein and an exit face through which said component beam paths leave said prism; and, two image-reversing roof prisms mounted on one of said faces so as to be offset relative to respective ones of said optical axes;

an optical deflecting element common to both of said component beam paths and being mounted on said pivot means for deflecting said component beams toward said sets of ocular optics, respectively, for all positions of said ocular optics within said angular range; and, said roof prisms being mounted on said exit face of said deflecting prism.

3. The binocular tube assembly of claim 2, said deflecting prism being a 60° deflecting prism mounted so as to receive both of said component beam paths from said stereomicroscope at said entry face; said exit face being directed toward said sets of ocular optics; said roof prisms being respective 90° roof prisms; and, said 90° roof prisms being cemented to said exit face so as to be offset relative to said optical axes, respectively.

4. The binocular tube assembly of claim 3, each of said 90° roof prisms being configured as a half-cube prism having a roof edge.

5. The binocular tube assembly of claim 2, said optical axes being spaced from each other at a first spacing, said roof prisms mounted on said exit face so as to cause said optical axes to be spaced from each other at a second spacing greater than said first spacing.

6. The binocular tube assembly of claim 2, said optical axes being spaced from each other at a first spacing, said assembly further comprising:

two rhombic prisms mounted along said component beam paths, respectively;

said rhombic prisms being disposed between said prism component group and a corresponding one of said sets of ocular optics; and, said rhombic prisms being rotatable about corresponding ones of said optical axes to adjust said spacing.

7. The binocular tube assembly of claim 2, said prism component group being mounted so as to remain stationary relative to said stereomicroscope as said sets of oculars are pivoted through said angular range.

8. The binocular tube assembly of claim 7, said optical deflecting element being rotatable through an angle interval of 25°.

9. The binocular tube assembly of claim 2, said pivot means comprising: a pivot joint defining a pivot axis; and, a housing pivotally connected to said pivot joint so as to be movable about said pivot axis through said angular range; said two sets of ocular optics, said prism component group and said optical deflecting element all being mounted in said housing so as to pivot through said angular range while maintaining a defined orientation relative to each other.

10. A binocular tube assembly for a stereomicroscope defining at least two stereoscopic component beam paths along first and second optical axes, respectively, said binocular tube assembly comprising:

two sets of ocular optics;

pivot means for pivotally mounting said sets of ocular optics to pivot relative to said stereomicroscope through a pregiven angular range;

a prism component group including a deflecting prism having an entry face for receiving said component beam paths therein and an exit face through which said component beam paths leave said prism; and, two image-reversing roof prisms mounted on one of said faces so as to be offset relative to respective ones of said optical axes;

an optical deflecting element common to both of said component beam paths and being mounted on said pivot means for deflecting said component beams toward said sets of ocular optics, respectively, for all positions of said ocular optics within said angular range; and, said roof prisms being mounted on said entry face of said deflecting prism.

11. The binocular tube assembly of claim 10, further comprising:

a base housing mounted on said stereomicroscope; said prism component group being mounted in said base housing so as to remain in a fixed orientation relative to said stereomicroscope;

said pivot means including: a pivot joint defining a pivot axis and being mounted on said base housing; a tube housing pivotally connected to said pivot joint so as to be movable about said pivot axis through said angular range; and, said two sets of ocular optics being mounted in said tube housing so as to be rotatable about said pivot axis with said housing and relative to said prism component group; and, said deflecting element being mounted on said pivot joint so as to be likewise rotatable relative to said prism component group.

12. The binocular tube assembly of claim 11, said deflecting element and said two sets of ocular optics being mounted in said tube housing so as to have a defined relative orientation to each other.

13. The binocular tube assembly of claim 12, wherein said stereomicroscope is utilized to view an object; and, wherein said deflecting element is mounted in said component beam paths and on said pivot joint so as to cause the component beam paths impinging on said deflecting element to be at least partially deflected back in the direction of the object.

14. The binocular tube assembly of claim 12, further comprising two rhombic prisms mounted in said tube housing in respective ones of said component beam paths; and, each of said rhombic prisms being disposed between said deflection element and the corresponding one of said sets of ocular optics.

15. The binocular tube assembly of claim 14, each of said rhombic prisms defining a longitudinal axis and being mounted in said tube housing so as to be rotatable about an axis perpendicular to said longitudinal axis.

* * * * *

UNITED STATES PATENT AND TRADEMARK OFFICE
CERTIFICATE OF CORRECTION

PATENT NO. : 5,589,977  
DATED : December 31, 1996  
INVENTOR(S) : Christian Lucke, et. al.

Page 1 of 3

It is certified that error appears in the above-indentified patent and that said Letters Patent is hereby corrected as shown below:

In column 1, line 16: delete "off" and substitute -- of -- therefor.

In column 1, line 28: delete "off" and substitute -- of -- therefor.

In column 1, line 57: delete "portoprisms" and substitute -- porroprisms -- therefor.

In column 2, line 8: delete "portoprisms" and substitute -- porroprisms -- therefor.

In column 2, line 58: delete "off" and substitute -- of -- therefor.

In column 3, line 6: delete "off" and substitute -- of -- therefor.

In column 3, line 8: delete "off" and substitute -- of -- therefor.

In column 3, line 13: delete "dr".

In column 3, line 46: delete "tile" and substitute -- the -- therefor.

In column 4, line 52: delete "Eotates" and substitute -- rotates -- therefor.

UNITED STATES PATENT AND TRADEMARK OFFICE
CERTIFICATE OF CORRECTION

PATENT NO. : 5,589,977
DATED : December 31, 1996
INVENTOR(S) : Christian Lucke, et. al.

It is certified that error appears in the above-indentified patent and that said Letters Patent is hereby corrected as shown below:

In column 4, line 57: delete "off" and substitute -- of -- therefor.

In column 5, line 15: delete "off" and substitute -- of -- therefor.

In column 6, line 17: delete "image" and substitute -- impinge -- therefor.

In column 6, line 24: delete "tile" and substitute -- the -- therefor.

In column 6, line 57: delete "s" and substitute -- is -- therefor.

In column 6, line 64: delete "tile" and substitute -- the -- therefor.

UNITED STATES PATENT AND TRADEMARK OFFICE
CERTIFICATE OF CORRECTION

PATENT NO. : 5,589,977
DATED : December 31, 1996
INVENTOR(S) : Christian Lucke, et. al.

It is certified that error appears in the above-indentified patent and that said Letters Patent is hereby corrected as shown below:

In column 7, line 27: delete "defelcting" and substitute -- deflecting -- therefor.

Signed and Sealed this

Eighth Day of April, 1997

Attest:

BRUCE LEHMAN

Attesting Officer

Commissioner of Patents and Trademarks